(12) United States Patent
Rodriguez Oquendo

(10) Patent No.: US 9,995,759 B2
(45) Date of Patent: *Jun. 12, 2018

(54) USE OF LYMPHOCYTE ACTIVATION GENE 3 (LAG-3) EXPRESSION PROFILING AS A BIOMARKER FOR ASSESSING INFLAMMASOMES, CHRONIC INFLAMMATORY DISEASES AND DYSFUNCTIONAL HDL

(71) Applicant: Annabelle Rodriguez Oquendo, Farmington, CT (US)

(72) Inventor: Annabelle Rodriguez Oquendo, Farmington, CT (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/689,547

(22) Filed: Apr. 17, 2015

(65) Prior Publication Data

US 2015/0355203 A1 Dec. 10, 2015

Related U.S. Application Data

(60) Provisional application No. 61/980,869, filed on Apr. 17, 2014.

(51) Int. Cl.
*G01N 33/92* (2006.01)

(52) U.S. Cl.
CPC ... *G01N 33/92* (2013.01); *G01N 2333/70596* (2013.01); *G01N 2800/24* (2013.01); *G01N 2800/2871* (2013.01); *G01N 2800/50* (2013.01)

(58) Field of Classification Search
None
See application file for complete search history.

(56) References Cited

PUBLICATIONS

Nabel et al., "Cardiovascular Disease," N. Eng. J. Med. 349:60-72 (2003).*
Macon-Lemaitre et al., "The negative regulatory function of the lymphocyte-activation gene-3 co-receptor (CD223) on human T cells," Immunol. 115:170-178 (2005).*
Golden et al., "Lymphocyte activation gene 3 and coronary artery disease," JCI Insight 1(17):e88628, pp. 1-15 (published online Oct. 2016).*
Sierro S, Romero P, Speiser DE. The CD4-like molecule LAG-3, biology and therapeutic applications, Expert Opin Ther Targets 2011;15:91-101.
[Kisielow M, Kisielow J, Capoferri-Sollami G, Karjalainen K. Expression of lymphocyte activation gene 3 (LAG-3) on B cells is induced by T cells. Eur J Immunol 2005; 35:2081-2088.
Baixeras E, Huard B, Miossec C, Jitsukawa S, Martin M, Hercend T, Auffray C, Triebel F, Piatier-Tonneau D., Characterization of the lymphocyte activation gene 3-encoded protein. A new ligand for human leukocyte antigen class II antigens, J. Exp. Med. 1992; 176:327-337.
Morales O, Mrizak D, Francois V, Mustapha R, Miroux C, Depil S, Decouvelaere AV, Lionne-Huyghe P, Auriault C, de Launoit Y, Pancre V, Delhem N. Epstein-Barr virus infection induces an increase of T regulatory type 1 cells in Hodgkin lymphoma patients. Br J Haematol Jul. 9, 2014. Epub ahead of print.
Woo S-R, Li N, Bruno TC, Forbes K, Brown S, Workman C, Drake CG, Vignali DAA. Differential subcellular localization of the regulatory T-cell protein LAG-3 and the coreceptor CD4. Eur. J. Immunol 2010;40:1768-1777.
Simons K, Toomre D. Lipid rafts and signal transduction. Nat Rev Mol Cell Biol 2000;1:31-39.
Schamel WW, Reth M. Monomeric and oligomeric complexes of the B cell antigen receptor. Immunity. 2000;13:5-14.
Takata M, Sabe H, Hata A, Inazu T, Homma Y, Nukada T, Yamamura H, Kurosaki T. Tyrosine kinases Lyn and Syk regulate B cell receptor-coupled Ca2+ mobilization through distinct pathways. EMBO J. 1994; 13:1341-9.
Blix ES, Irish JM, Husebekk A, Delabie J, Forfang L, Tierens AM, Myklebust JH, Kolstad A. Phospho-specific flow cytometry identifies aberrant signaling in indolent B-cell lymphoma. BMC Cancer 2012;12:478.
Coggeshall KM, McHugh JC, Altman A. Predominant expression and activation-induced tyrosine phosphorylation of phospholipase C-gamma 2 in B lymphocytes. Proc Natl Acad Sci U S A. 1992; 89:5660-4.
Sugawara H, Kurosaki M, Takata M, Kurosaki T. Genetic evidence for involvement of type 1, type 2 and type 3 inositol 1,4,5-trisphosphate receptors in signal transduction through the B-cell antigen receptor. EMBO J. 1997; 16:3078-88.
Hyka N, Dayer J-M, Modoux C, Kohno T, Edwards III CK, Roux-Lombard P, Burger D. Apolipoprotein A-I inhibits the production of interleukin-1β and tumor necrosis factor-α by blocking contact-mediated activation of monocytes by T lymphocytes. Blood 2001;97:2381-2389.
"Association of SCARB1 variatns with subclinical atherosclerosis and incident cardiovascular disease: the multi-ethnic study of atherosclerosis" Manichaikul et al. Arterioscler Vasc Biol 2012; 32:1991-1999.

* cited by examiner

*Primary Examiner* — Julie Ha
*Assistant Examiner* — Kristina M Hellman
(74) *Attorney, Agent, or Firm* — Royal W. Craig; Baker Donelson, PC

(57) ABSTRACT

A method for determining whether a subject has or is predisposed to abnormal expression of inflammasomes and/or to dysfunctional HDL suitable for use in diagnosing atherosclerosis, chronic inflammatory disease, Incident Cardiovascular Disease (ICD) and other pathologies characterized by an inflammatory response. Specifically, a protein assay that measures LAG-3 can be used as a diagnostic predictor of pathologies such as infection, inflammation, chronic inflammatory disease, and coronary artery disease. The diagnostic is combined with the therapeutic use of a remediating drug for treatment.

17 Claims, 14 Drawing Sheets

Table 1. Study demographics of HALP population.

| | |
|---|---|
| Age (yrs, mean ± SD, [range]) | 52.8 ± 13.0 [18-81] |
| Race (n, %) | |
| White | 107 (75%) |
| Black | 23 (16%) |
| Asian | 7 (5%) |
| Hispanic | 6 (4%) |
| Gender (n, %) | |
| Male | 26 (18%) |
| Female | 118 (82%) |
| Total cholesterol (mg/dl, [range]) | 213 ± 37 [123-295] |
| Triglycerides (mg/dl) | 75 ± 32 [27-209] |
| LDL-C (mg/dl) | 114 ± 31 [49-195] |
| HDL-C (mg/dl) | 84 ± 20 [60-156] |
| pLAG-3 (pg/ml, mean ± SE, [range]) | 8,882 ± 10,426 [0-58,646] |
| rs10846744 (n, %) | |
| GG | 98 (70%) |
| CG | 22 (15%) |
| CC | 22 (15%) |

Table 2. Differential transcriptional regulation of gene targets in risk C expressing EBV-transformed B lymphocytes: cis and trans.

| Downregulated cis | Fold-change | Upregulated cis | Fold-change |
|---|---|---|---|
| Lymphocyte activation gene 3 | 5 | Carboxypeptidase M | 4 |
| Aldehyde dehydrogenase 1 family member L2 | 4 | Tescalcin | 4 |
| Inhibin beta C | 3 | Glycosyltransferase 1 domain containing 1 | 3 |
| WD repeat domain 6 | 3 | | |
| Fatty acyl CoA reductase | 2 | | |

| Downregulated trans | Fold-change | Upregulated trans | Fold-change |
|---|---|---|---|
| MHC class II | 82 | LAIR1 (leukocyte associated Ig-like receptor 1) | 274 |
| Mediator complex subunit 12-like | 6 | ABP1 (amine oxidase copper containing 1) | 115 |
| Protein tyrosine phosphatase | 3 | P2RX2 (purinergic receptor) | 16 |
| Nitric oxide synthase 3 | 3 | NR2F2 (nuclear receptor subfamily 2, group F member 2) | 7 |
| Lymphocyte transmembrane adaptor 1 | 2 | NLRP3 (NLR family) | 5 |

FIG. 3

USE OF LYMPHOCYTE ACTIVATION GENE 3 (LAG-3) EXPRESSION PROFILING AS A BIOMARKER FOR ASSESSING INFLAMMASOMES, CHRONIC INFLAMMATORY DISEASES AND DYSFUNCTIONAL HDL

CROSS-REFERENCE TO RELATED APPLICATION

This application claims the benefit under 35 U.S.C. § 119(e) of U.S. Provisional Application Ser. No. 61/980,869, filed 17 Apr. 2014, and U.S. application Ser. No. 13/707,256 filed Dec. 6, 2012, both of which are incorporated herein by reference.

STATEMENT REGARDING FEDERALLY FUNDED RESEARCH

This invention was made with government support under Grant No. R01HL075646 awarded by the National Institutes of Health. The government has certain rights in the invention.

BACKGROUND OF THE INVENTION

1. Field of the Invention

The present invention relates to disease detection and treatment for diseases such as cardiovascular and immune diseases and, more specifically, to a method for using lymphocyte activation gene 3 (LAG-3) profiling as a biomarker for assessing inflammasomes, chronic inflammatory diseases and dysfunctional HDL.

2. Description of the Background

The lipoprotein receptor, scavenger receptor class B type 1 (SR-BI), is a physiologically relevant receptor that modulates cholesterol levels, especially HDL-cholesterol (HDL-C), in mice and humans. In co-pending U.S. application Ser. No. 13/707,256 filed Dec. 6, 2012, the present inventor disclosed a method of genotyping women in order to identify the presence of the rs10846744 mutation of the SCARB1 gene (located on chromosome 12:q24.32). This was significantly associated with infertility, as well as subclinical atherosclerosis (SCA) and incident cardiovascular disease (CVD) in male participants of the Multi-Ethnic Study of Atherosclerosis (MESA). Specifically, carriers of the risk C allele had significantly increased odds for incident CVD, and in a multivariate regression model this relationship was not attenuated by inclusion of traditional CVD risk factors such as age, body mass index, hypertension, smoking, renal disease, or lipid levels (whether total cholesterol, LDL-cholesterol [LDL-C], HDL-C, or triglycerides). These findings strongly suggested that other factors or pathways might be causal in the association of this genetic variant with incident CVD.

Interestingly, rs10846744 resides within the first intron of SCARB1 and bioinformatic analysis revealed that this single nucleotide polymorphism (SNP) resides within a regulatory region. The data suggested that this SNP could transcriptionally regulate genes on the same chromosome (intra-chromosomal) or inter-chromosomally. The present inventor investigated this possibility and a number of transcriptionally regulated gene candidates emerged. One in particular, lymphocyte activation gene-3 (LAG-3) is also located on chromosome 12 and was investigated further.

In vitro and ex vivo approaches were taken to examine the association of rs10846744 with LAG-3 in biospecimens isolated from hyperalphalipoproteinemic (HALP) women and men subjects. It was found that rs10846744 is significantly associated with alterations in the expression and function of LAG-3, and markers of intracellular inflammasomes.

LAG-3 is located near the CD4 loci on chromosome 12 (chr 12:p13) while rs10846744 is located on chr12:q24.32. LAG-3 has a similar function, if not a competitive one against CD4, by binding MHC class II on antigen presenting cells. [Sierro S, Romero P, Speiser D E. The CD4-like molecule LAG-3, biology and therapeutic applications, Expert Opin Ther Targets 2011; 15:91-101] in murine cells. Kisielow et al reported that activated T cells induced LAG-3 expression on B cells. [Kisielow M, Kisielow J, Capoferri-Sollami G, Karjalainen K. Expression of lymphocyte activation gene 3 (LAG-3) on B cells is induced by T cells. Eur J Immunol 2005; 35:2081-2088] They determined that LAG-3 induction on B cells was T cell dependent and not dependent on other stimuli such as unmethylated CpG motif 1826, bacterial LPS, or anti-Ig antibody in combination with anti-CD40 and IL-4. In contrast, LAG-3 RNA and protein was detected in EBV-transformed B cells, with significantly higher expression in EBV-transformed cells expressing the reference G allele as compared with cells expressing the risk C allele. Although EBV transformation of B lymphocytes could activate the cells, there was a significant difference in the level of LAG-3 expression based on rs10846744 genotype stratification. Importantly, others observed a lack of LAG-3 expression in B cells, such as Ramos cells [Baixeras E, Huard B, Miossec C, Jitsukawa S, Martin M, Hercend T, Auffray C, Triebel F, Piatier-Tonneau D., Characterization of the lymphocyte activation gene 3-encoded protein. A new ligand for human leukocyte antigen class II antigens, J. Exp. Med. 1992; 176:327-337] However, the present inventor genotyped these cells and found that they were heterozygous for the rs10846744 variant. More recently, Morales et al. showed that EBV positivity in Hodgkin lymphomas were significantly associated with increased gene expression of LAG-3. [Morales O, Mrizak D, Francois V, Mustapha R, Miroux C, Depil S, Decouvelaere A V, Lionne-Huyghe P, Auriault C, de Launoit Y, Pancre V, Delhem N. Epstein-Barr virus infection induces an increase of T regulatory type 1 cells in Hodgkin lymphoma patients. Br J Haematol 2014 Jul. 9, Epub ahead of print]

Baixeras et al., supra, characterized the cellular distribution of LAG-3 in a number of cell lines and demonstrated that LAG-3 resided within lipid rafts. Subsequently, Woo et al. reported the intracellular distribution of LAG-3 and found that LAG-3 was equally distributed between intracellular compartments and the plasma membrane. [Woo S-R, Li N, Bruno T C, Forbes K, Brown S, Workman C, Drake C G, Vignali D A A. Differential subcellular localization of the regulatory T-cell protein LAG-3 and the coreceptor CD4. Eur. J. Immunol 2010; 40:1768-1777] By using flow cytometry, the present inventor confirmed that low levels of LAG-3 were detected on the cell surface of risk C expressing cells regardless of stimulation conditions. However, LAG-3 was expressed on the cell surface in unstimulated reference G cells and its levels decreased significantly after stimulation, due to cleavage of cell surface LAG-3 by metalloproteases. These results in EBV transformed B cells are in contrast to those reported by Woo et al., supra, in that they reported that LAG-3 was expressed on the surface only in activated T cells.

It is also known that lipid raft signaling is essential for B cell activation. [Simons K, Toomre D. Lipid rafts and signal transduction. Nat Rev Mol Cell Biol 2000; 1:31-39] Specifically, stimulation of the B cell receptor (BCR) initiates phosphorylation of the immunoreceptor tyrosine-based activation motifs (ITAMs) in the cytoplasmic tails of CD79A and CD79B (transmembrane immunoglobulin (Ig) receptor associated with Ig-alpha/Ig-beta heterodimers). [Schamel W W, Reth M. Monomeric and oligomeric complexes of the B cell antigen receptor. Immunity. 2000; 13:5-14] Phosphorylation of ITAMs serve as docking sites for Syk, which is mediated by different Src family kinases (SFKs) including Fyn, Blk, and Lyn. [Takata M, Sabe H, Hata A, Inazu T, Homma Y, Nukada T, Yamamara H, Kurosaki T. Tyrosine kinases Lyn and Syk regulate B cell receptor-coupled Ca2+ mobilization through distinct pathways. EMBO J. 1994; 13:1341-9] Lyn is the major protein involved in lipid raft signaling upon B cell activation [Simons, supra]. This activation initiates the coordinate assembly of the "signalosome", composed of a variety of intracellular signaling molecules and includes Btk, phosphatidylinositol 3-kinase (PI3K) and PLCγ2. [Blix E S, Irish J M, Husebekk A, Delabie J, Forfang L, Tierens A M, Myklebust J H, Kolstad A. Phospho-specific flow cytometry identifies aberrant signaling in indolent B-cell lymphoma. BMC Cancer 2012; 12:478] PLCγ2 is the predominant isoform expressed in human B lymphocytes. [Coggeshall K M, McHugh J C, Altman A. Predominant expression and activation-induced tyrosine phosphorylation of phospholipase C-gamma 2 in B lymphocytes. Proc Natl Acad Sci USA. 1992; 89:5660-4] It is also indispensable for BCR-mediated phosphoinositol hydrolysis and the subsequent biochemical events including PKC activation. [Sugawara H, Kurosaki M, Takata M, Kurosaki T. Genetic evidence for involvement of type 1, type 2 and type 3 inositol 1,4,5-trisphosphate receptors in signal transduction through the B-cell antigen receptor. EMBO J. 1997; 16:3078-88]

However, the major apolipoprotein associated with HDL particles, apoA-I, has been shown to inhibit inflammatory cytokine production by inhibiting activation of monocytes by T lymphocytes. [Hyka N, Dayer J-M, Modoux C, Kohne T, Edwards III C K, Roux-Lombard P, Burger D. Apolipoprotein A-I inhibits the production of interleukin-1β and tumor necrosis factor-α by blocking contact-mediated activation of monocytes by T lymphocytes. Blood 2001; 97:2381-2389] Specifically, Hyka et al. observed that apoA-I inhibited cytokine production from stimulated monocytes by first binding to a surface factor, which suggests the possibility that apoA-I might interact with surface LAG-3.

The significant association of SCARB1 variant, rs10846744, with coronary heart disease (CHD) was shown in Manichaikul et al. [Arterioscler Thromb Vasc Biol 2012; 32:1991-1999]. However, previous analyses do not show that rs10846744 is directly associated with SCA and incident CVD. This is because, as the present inventor has found, LAG-3 is an important immune regulator that mediates the association of rs10846744 with atherosclerotic disease and CVD. Based on that mediator role that LAG-3 plays in CVD and other chronic inflammatory diseases, a method is herein disclosed for using LAG-3 expression profiling as a biomarker for assessing inflammasomes, chronic inflammatory diseases and dysfunctional HDL.

SUMMARY OF THE INVENTION

It is, therefore, an object of the present innovation to provide a novel strategy for using LAG-3 expression profiling as a biomarker for assessing inflammasomes, chronic inflammatory diseases and dysfunctional HDL, followed by a tailored therapeutic regimen to remediating said diseases. The LAG-3 expression may be profiled by either SCARB1 rs10846744 genotyping and/or HDL particle measurement by 2D gel electrophoresis as described below. In one embodiment, the method comprises a first step of pre-screening a subject for one or more risk factors for developing cardiovascular disease, a second step of detecting a level of soluble lymphocyte activation gene 3 (sLAG-3) in a sample from the subject by SCARB1 rs10846744 genotyping and/or HDL particle measurement), a third step of comparing the level of sLAG-3 in the sample with the level of sLAG-3 in a control sample, a fourth step of detecting a decrease in the level of sLAG-3 which indicates that the subject has an increased risk of developing atherosclerosis or a cardiovascular disease, and a fifth step of treating the subject with a therapeutic amount of one or more agents selected from the group consisting of a recombinant LAG-3 protein (e.g., a recombinant soluble dimeric form of LAG-3 (sLAG-3-Ig, IMP321), an anti-inflammatory agent, an agent that improves HDL-C function in the subject and an agent that decreases dysfunctional HDL-C in the subject.

Other objects, features, and advantages of the present invention will become more apparent from the following detailed description of the preferred embodiments and certain modifications thereof.

BRIEF DESCRIPTION OF THE DRAWINGS

Other objects, features, and advantages of the present invention will become more apparent from the following detailed description of the preferred embodiments and certain modifications thereof when taken together with the accompanying drawings in which:

FIG. 3 comprises two tables: Table 1 shows the population of HALP subjects for Example 1; and Table 2 shows the differential transcriptional regulation of gene targets in risk C expressing EBV-transformed B lymphocytes: cis and trans.

DETAILED DESCRIPTION OF THE PREFERRED EMBODIMENT

Figure 1:
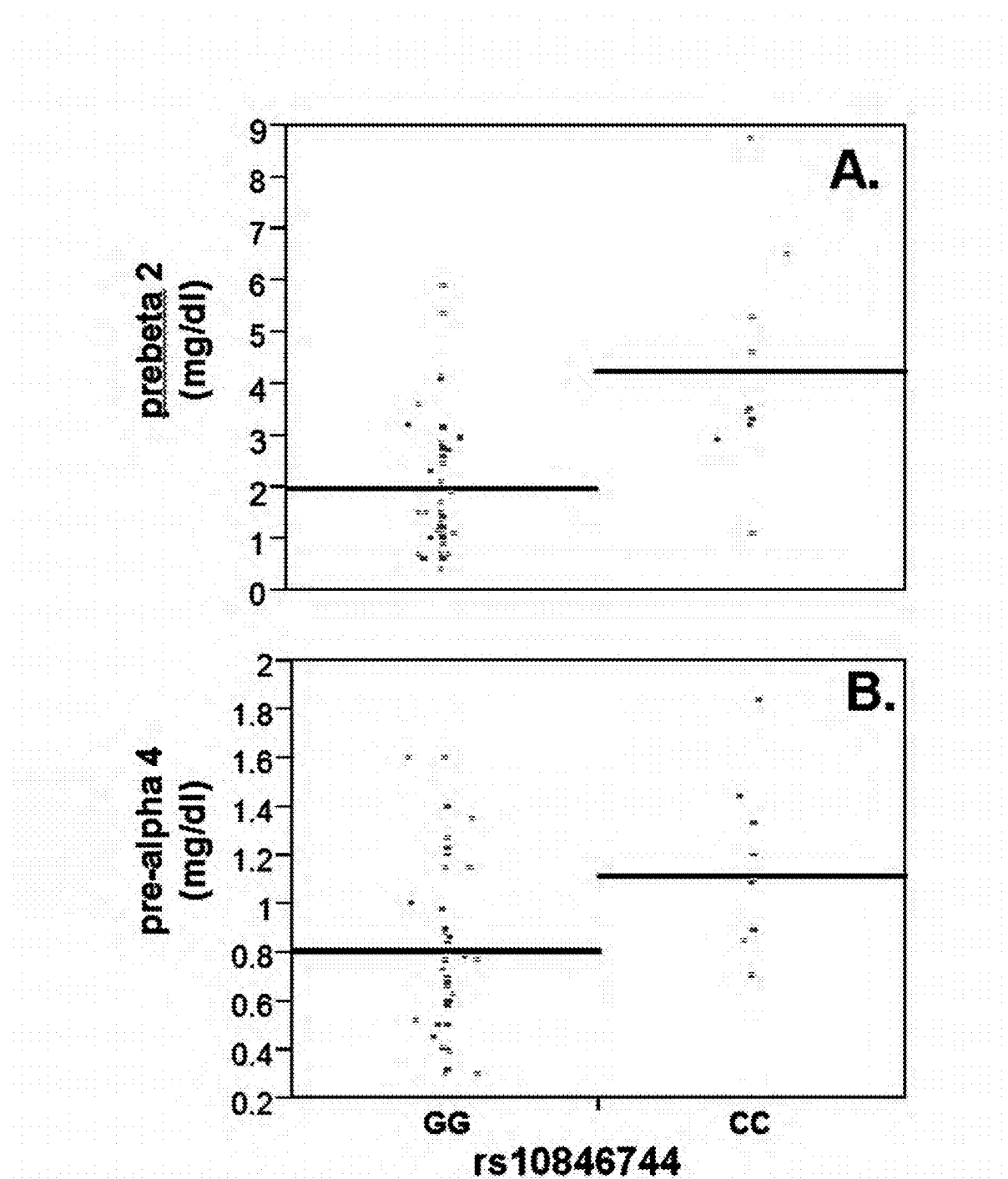
FIG. 1 is a graph of the association of rs10846744 with small HDL particles pre-beta 2 (panel A) and pre-alpha 4 (panel B) mg/dl as measured by 2D gel electrophoresis.

The present invention provides novel methods and kits for determining whether a subject has or is predisposed to abnormal expression of inflammasomes and/or to dysfunctional HDL. The assays are good diagnostics for atherosclerosis, chronic inflammatory disease, Incident Cardiovascular Disease (ICD) and other pathologies characterized by an inflammatory response. Specifically, the SNP rs10846744 is a noncoding SNP in the SCARB1 gene that affects the transcription of the LAG-3 gene. The SNP rs10846744 can be used as a diagnostic predictor of pathologies such as infection, inflammation, chronic inflammatory disease, and coronary artery disease. The diagnostic is combined with the therapeutic use of a remediating small molecule drug or biological agent for treatment it will be understood that the present invention is not limited to the particular methods and components, etc., described herein, as these may vary.

As used herein, the singular forms "a," "an," and "the" include the plural reference unless the context clearly dictates otherwise. Thus, for example, a reference to a "protein" is a reference to one or more proteins, and includes equivalents thereof known to those skilled in the art. Any and all references to a SNP by the "rs" designation, for example rs10846744 hereby incorporates the associated nucleotide sequence which is easily retrievable by known methods. Specifically, the nucleotide sequence for rs10846744 is retrievable, for example, from NCBI's dbSNP Entrez database.

LAG-3 is Transcriptionally Controlled by the rs10846744 Variant

RNA sequencing was used to identify the immune modulator LAG-3 as playing a major role in the causal pathway linking the association of the SCARB1 intronic variant, rs10846744, with subclinical atherosclerosis and incident CVD. Validation experiments confirmed the significant association of SCARB1 rs10846744 with LAG-3. The experiments observed significantly lower levels of sLAG-3 in the culture media from risk C expressing cells as compared to the reference G cells. Thus, the different methodologies confirmed that less LAG-3 was expressed in the risk C cells. We then examined what effect, if any, the lack of LAG-3 might have on the downstream signaling pathway in EBV-transformed B cells. Our results clearly showed significant differences in lipid raft signaling between C and G expressing cells. The observation that we do not detect phosphorylation of CD79A in the rs10846744 C risk allele indicates that impairment of LAG-3 to the membrane inhibits the interaction between the receptors initiating proximal and downstream signaling, further indicating the important role of LAG-3 in B cell activation. Importantly, overexpressing or silencing LAG-3 confirmed the central role of LAG-3 in downstream signaling. Combining data derived from RNA-sequencing and the in vitro studies of LAG-3 from the EBV-transformed B cells, and with the knowledge that surface LAG-3 was cleaved to generate sLAG-3, the present inventor explored whether plasma sLAG-3 levels would be significantly different between carriers of the rs10846744 variant.

FIG. 9(A) shows a significant difference in plasma sLAG-3 levels between HALP carriers of the reference G vs. risk C allele, while FIG. 9(B) shows significantly lower plasma LAG-3 levels in African-Americans compared with Caucasians, regardless of genotype. Within the field of atherosclerosis there was no previous associations of HDL lipoproteins and/or subtractions with LAG-3 or sLAG-3. We did not observe an association of plasma apoA-I with rs10846744 or sLAG-3 but did find a significant association of these variables with small HDL particles. Small dense HDL particles, which are enriched in apoA-I and cholesterol poor, have been positively associated with increased risk for CHD in a number of large clinical studies.

Cellular LAG-3 expression and function were significantly reduced in cells isolated from carriers of the risk C allele. More importantly, circulating sLAG-3 levels were significantly lower in these same carriers as measured in the HALP. In conclusion, we identified LAG-3 an important immune regulator, as being transcriptionally controlled by the rs10846744 variant.

Diagnostic Method #1

Generally, an embodiment of the present method entails symptomatic diagnosis, and a two-stage genetic screening of a biological sample from a subject for the presence of specific allelic variants of one or more polymorphic regions of an SR-BI gene conducted to determine the presence of the underlying SCARB1 mutation rs10846744. SR-B1 (SCARB1) is the predominant receptor for HDL cholesterol and plays an important role in reverse cholesterol transport (removal from cells with eventual disposal via the liver). SR-B1 is highly expressed in the liver and steroidogenic tissues such as the ovary. SR-B1 is thought to be critical in maintaining cholesterol stores for steroid production.

Figure 2:
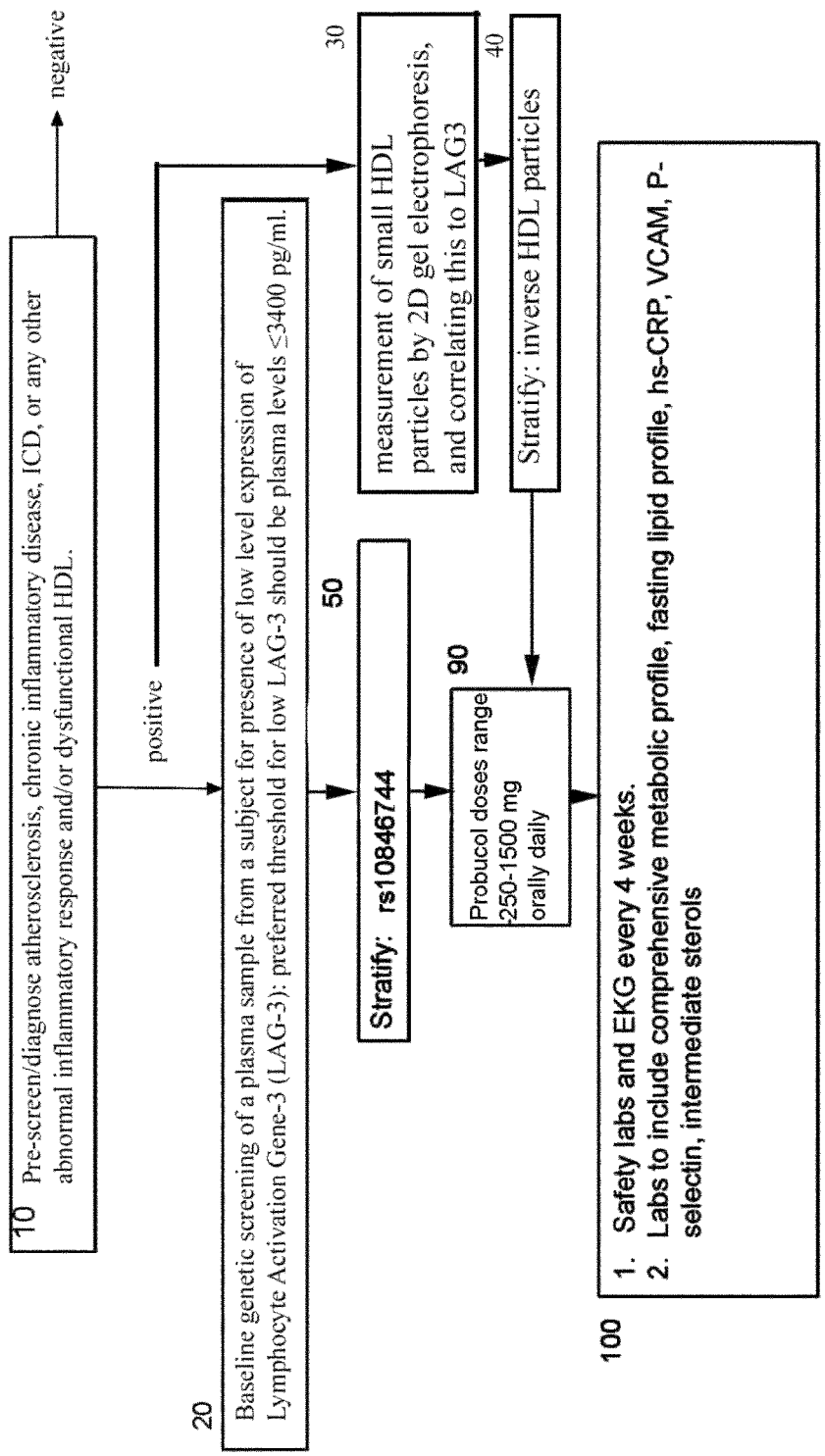
FIG. 2 is a block diagram of an exemplary embodiment of the present diagnostic method.

FIG. 2 is a block diagram of the present diagnostic method, which begins at step 10 with an initial pre-screening/diagnosis of a subject for atherosclerosis, chronic inflammatory disease, Incident Cardiovascular Disease (ICD) or any other pathology characterized by an inflammatory response, abnormal expression of inflammasomes and/or dysfunctional HDL.

Given an initial positive pre-screening, at step 20 diagnostic method #1 entails a baseline screening of a plasma sample from a subject for presence of low level expression of Lymphocyte Activation Gene-3 (LAG-3). LAG-3 expression is measured and low LAG-3 should be plasma levels≤3400 pg/ml. This LAG-3 expression profiling provides as positive biomarker for further assessment of inflammasomes, chronic inflammatory diseases and dysfunctional HDL. The LAG-3 expression profiling may or may not be used to stratify patients on the basis of their underlying SCARB1 mutation. The proinflammatory state of the risk C cells due to LAG-3 deficiency provides a novel protein biomarker for diseases associated with chronic inflammation, including autoimmune disease, atherosclerosis, type 2 diabetes mellitus, and Alzheimer's disease.

At step 50, and given the suspected presence of the rs10846744 SCARB1 mutation, the patient's underlying rs10846744 SCARB1 mutation is genetically confirmed. The presence of the rs10846744 SCARB1 mutation can be confirmed by a variety of known methods including genotyping. Genotyping for rs10846744 may be carried out by direct mutation analysis by DNA sequencing of a standard blood test. Genomic DNA is prepared from a whole blood sample purified to isolate DNA from the blood sample. The purity and quantity of DNA may be checked by spectrophotometry. The DNA is added to a plate and genotyped with an oligo-ligation assay (for example, SNPlex® is a suitable platform for SNP genotyping sold by Applied Biosystems of Foster City, Calif., USA) following manufacturer guidelines. The oligo-ligation assay uses fluorescent dye-labeled probes to indicate presence of the rs10846744 mutation. Other methods useful in screening for the presence of a specific allelic variant of one more polymorphic regions of a SR-BI gene include, for example, DNA sequencing, hybridization techniques, PCR based assays, fluorescent dye and quenching agent-based PCR assay (Taqman PCR detection system), RFLP-based techniques, single strand conformational polymorphism (SSCP), denaturating gradient gel electrophoresis (DGGE), temperature gradient gel electrophoresis (TGGE), chemical mismatch cleavage (CMC), heteroduplex analysis based system, techniques based on mass spectroscopy, invasive cleavage assay, polymorphism ratio sequencing (PRS), microarrays, a rolling circle extension assay, HPLC-based techniques, DHPLC-based techniques, oligonucleotide extension assays (OLA), extension based assays ARMS (Amplification Refractory Mutation System), ALEX (Amplification Refractory Mutation Linear Extension), SBCE (Single base chain extension), a molecular beacon assay, invader (Third wave technologies), a ligase chain reaction assay, nuclease assay-based techniques, hybridization capillary array electrophoresis (CAE), pyrosequencing, protein truncation assay (PTT), immunoassays, haplotype analysis, and solid phase hybridization (dot blot, reverse dot blot, chips), etc. One type of screening method is allele specific hybridization using probes overlapping the polymorphic site and having about 5, 10 20, 25, or 30 nucleotides around the polymorphic region. In one embodiment of the invention, several probes capable of hybridizing specifically to allelic variants are attached to a solid phase support, e.g., a "chip". Oligonucleotides can be bound to a solid support by a variety of processes, including lithography. Indeed, a chip can hold up to 250,000 oligonucleotides (GeneChip®, Affymetrix®). In one embodiment, a chip comprises all the allelic variants of at least one polymorphic region of a SR-BI gene. The solid phase support is then contacted with a test nucleic acid and hybridization to the specific probes is detected. Accordingly, the identity of numerous allelic variants of one or more genes can be identified in a simple hybridization experiment. In some screening methods it is necessary to first amplify at least a portion of a SR-BI gene prior to identifying the allelic variant. Amplification can be performed, e.g., by PCR, according to methods known in the art. In one embodiment genomic DNA of a cell is exposed to two PCR primers and amplification for a number of cycles sufficient to produce the required amount of amplified DNA. Because SNPs constitute sites of variation flanked b regions of invariant sequence, their analysis requires no more than the determination of the identity of the single nucleotide present at the site of variation and it is unnecessary to determine a complete gene sequence for each patient. Several methods have been developed to facilitate the analysis of such single nucleotide polymorphisms. The methods described herein may be performed, for example, by utilizing pre-packaged diagnostic kits, such as those described above, comprising at least one probe or primer nucleic acid described herein, which may be conveniently used, e.g., to determine whether a subject has or is at increased risk of developing a disease associated with a specific SR-BI allelic variant. The methods of the present invention, including methods for identifying the presence of an allelic variant or SNP in the SR-BI gene of a subject may be combined with other information or parameters using the methods well known in the art to aid in the identification of subject with deficiency in the SR-BI protein.

Diagnostic Method #2

Figure 11:
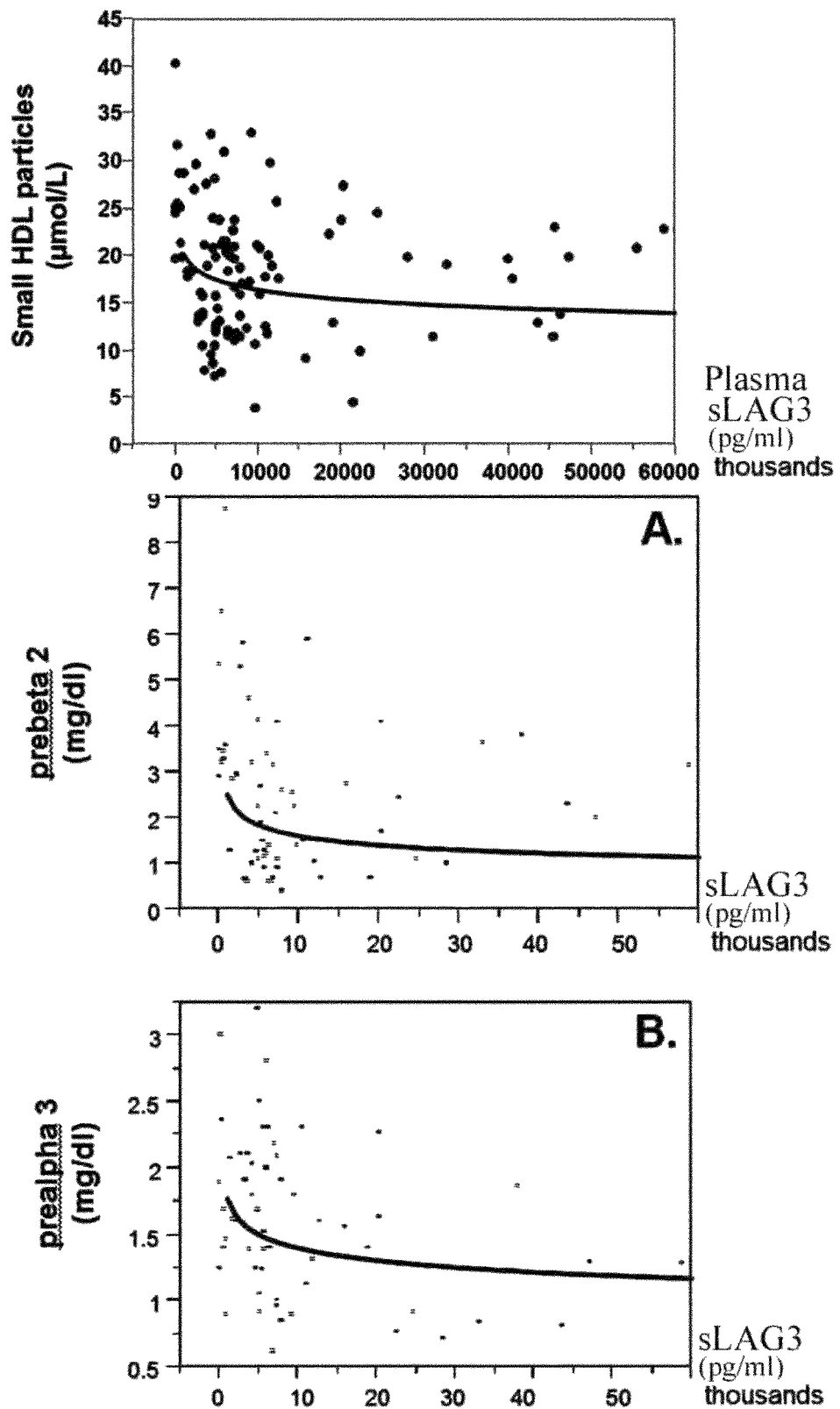
FIG. 11 is a composite of graph showing sLAG-3 significantly associated with small HDL particles by NMR spectroscopy (A), and associated with prebeta-2 HDL by 2D gel electrophoresis (B) and prealpha-4 small HDL particles by 2D gel electrophoresis (C). The inverse association of small HDL particles with sLAG-3 provides an alternative approach for LAG-3 expression profiling independent of SCARB1 rs10846744 genotyping, yet likewise effective as a biomarker for assessing inflammasomes, chronic inflammatory diseases and dysfunctional HDL.

FIG. 11 shows sLAG-3 significantly associated with small HDL particles by 2D gel electrophoresis and NMR spectroscopy. sLAG-3 levels were inversely associated with small HDL particles in fasting plasma samples from HALP subjects. This data was not stratified by carrier status for rs10846744, P=0.01, r=0.27, n=81. This illustrates an alternative method for LAG-3 expression profiling independent of SCARB1 rs10846744 genotyping. Thus, the FIG. 2 step 20 baseline screening of a plasma sample from a subject for presence of low level expression of Lymphocyte Activation Gene-3 (LAG-3) may instead be conducted at step 30 by measurement of small particles by 2D gel electrophoresis or NMR spectroscopy, and correlating this to LAG-3. As above, LAG-3 expression is measured and low LAG-3 should be plasma levels≤3400 pg/ml. This inverse increase in small HDL particles with low level LAG-3 expression profiling likewise provides a positive biomarker for further assessment of inflammasomes, chronic inflammatory diseases and dysfunctional HDL. The FIG. 2 step 50 stratification would be replaced by the small HDL particle stratification as a positive biomarker at step 40. Small HDL particles can be measured by a number of methodologies, including 2D gel electrophoresis, NMR spectroscopy, and gradient centrifugation.

Given confirmation by SCARB1 is 10846744 genotyping and/or HDL particle measurement by 2D gel electrophoresis, at step 90 the present method initiates a therapeutically-effective regimen of the cholesterol medication probucol, or administering a statin or other cholesterol/lipoprotein altering medication alone or recombinant LAG-3 alone or anti-inflammatory/anti-oxidant alone or in combination with Probucol and/or statin or other cholesterol/lipoprotein altering medication. Treatment strategies used in combination with the LAG-3 diagnostic testing include state-of-the-art therapies related to autoimmune diseases, atherosclerosis, type 2 diabetes mellitus and Alzheimer's disease. For example, the present method initiates therapeutically-effective regimens of the cholesterol medication probucol at step 30. An exemplary regimen of probucol treatment may comprise a lifetime of low-dose treatment (within a range of from 250 mg/day to 1000 mg/day). Finally, at step 100 monitoring comprises monthly safety labs, and prior to FDA approval should include comprehensive profiles and EKGs, all to determine effect on LDL oxidation and on plasma-HDL cholesterol. One skilled in the art will readily understand that other suitable therapeutic strategies may be employed to treat these genetically screened individuals including, but not limited to, any other cholesterol and triglyceride modifying medications, progestational and estrogen and estrogen-like medications, as well as medications similar to probucol for lowering HDL cholesterol levels and as antioxidants.

Without further elaboration, it is believed that one skilled in the art, using the preceding description, can utilize the present invention to the fullest extent. To ensure this, an example is given below.

EXAMPLE 1

Materials and Methods

Community dwelling adults between the ages of 18-80 years with fasting plasma HDL-C levels≥60 mg/dl (HALP)

were enrolled in a clinical study. The population was middle-aged and predominantly white females. At the time of enrollment none of the study subjects were treated with cholesterol lowering medications whether prescribed or over-the-counter. Subjects consented to provide overnight fasting blood samples for analysis of lipid profile, DNA analysis for SCARB1 genotyping, and lymphocyte isolation from buffy coats. One-way analysis of variance was used for multiple comparisons of categorical covariates, and Student's t-test for two sample analysis. To assess the effect of time as a continuous variable, quadratic polynomial regressions were performed with time as the dependent factor. Probability values≤0.05 were considered statistically significant. The frequency of the homozygous rs10846744 variant was similar to rates previously described in Multi-Ethnic Studies of Atherosclerosis (MESA). Transcriptome analysis reveals differential expression of LAG-3. Since rs10846744 resides within a regulatory region of SCARB1 as shown by a bioinformatic screen of the ENCODE database [Encyclopedia of DNA Elements available at University of California, Santa Cruz], we first examined whether transcriptional differences existed between the reference G and the risk C allele expressing B cells cultured under basal (unstimulated) conditions. Since rs10846744 is on the long arm of chromosome 12 we examined for transcriptional differences of targets also residing on chromosome 12 (cis). Five gene transcripts were significantly downregulated and 3 gene transcripts upregulated in risk C cells as compared with the reference G cells (See FIG. 3, Table 2). In addition to transcriptome differences on chromosome 12, we also observed inter-chromosomal transcriptional differences (FIG. 3, Table 2) that included significant up-regulation of intracellular inflammasome markers, such as NLRP3 (trans). LAG-3 expression is significantly lower in risk C expressing cells. In order to measure changes in cell surface LAG-3 expression following activation, cells were first incubated with and without phorbol myristate acetate (PMA)/ionomycin+interleukin-4 (IL-4) and then LAG-3 was measured by flow cytometry.

Figure 4:
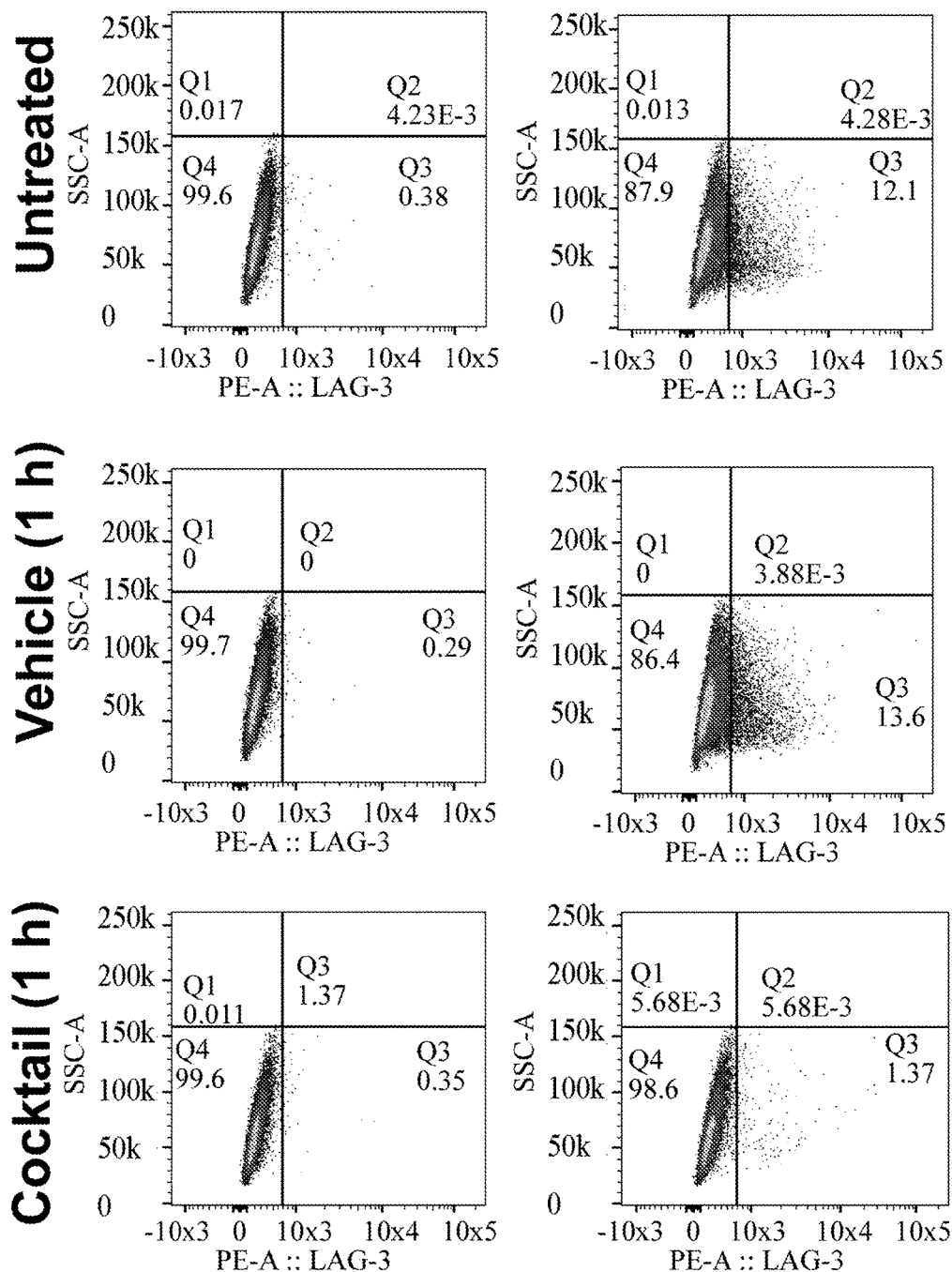
FIG. 4 is a series of flow cytograms showing the differential cell surface expression of LAG-3 as measured by flow cytometry in reference G (Panel 1) and risk C (Panel 2) expressing cells. The results are shown in the absence or presence of stimulation for 0-4 hours.
Figure 4:
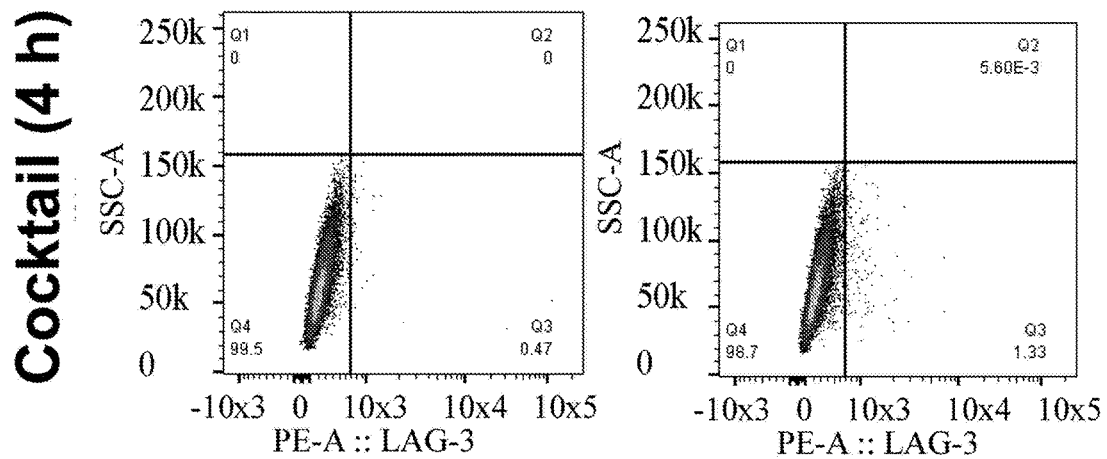
Figure 4:
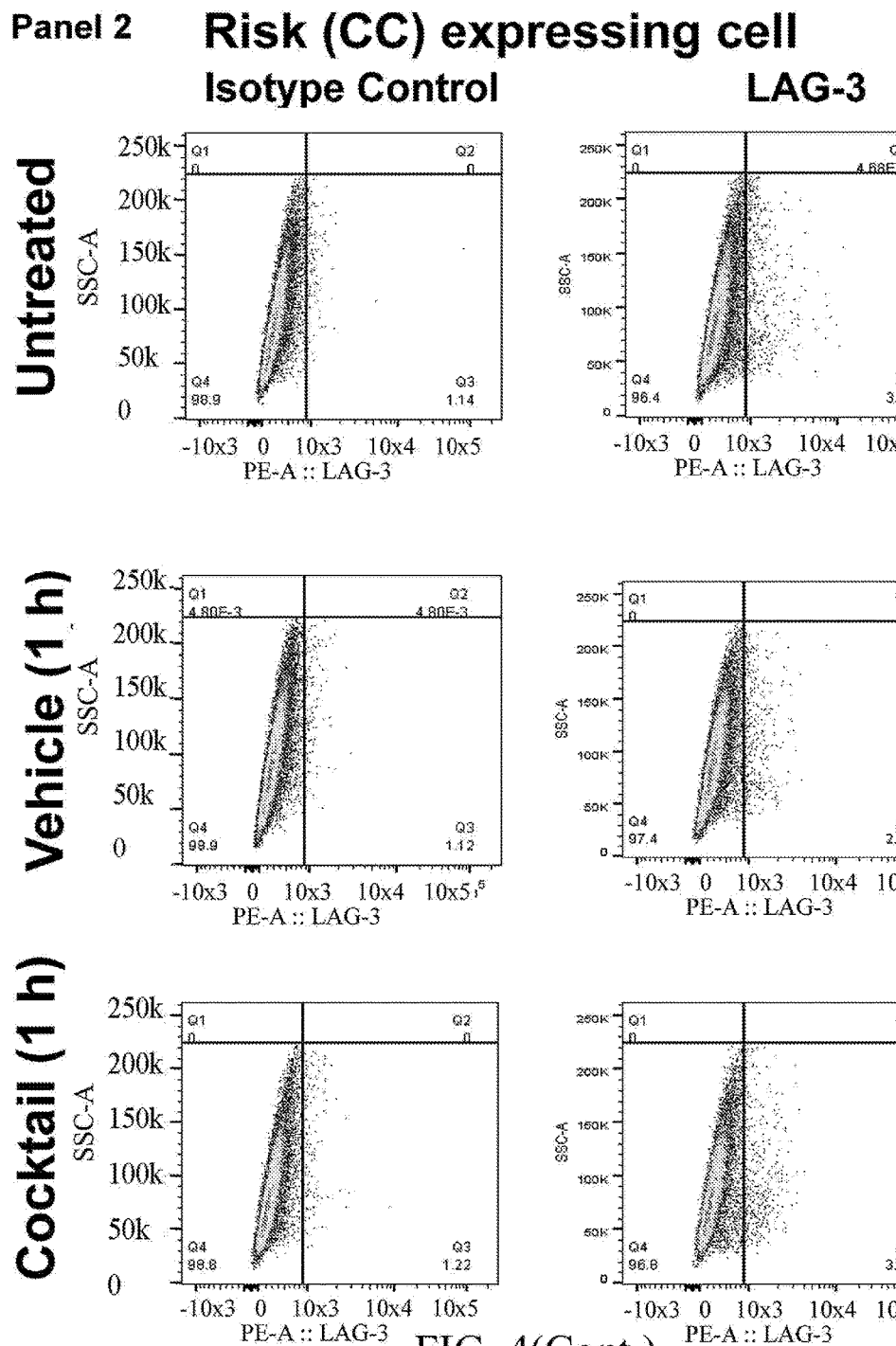
Figure 4:
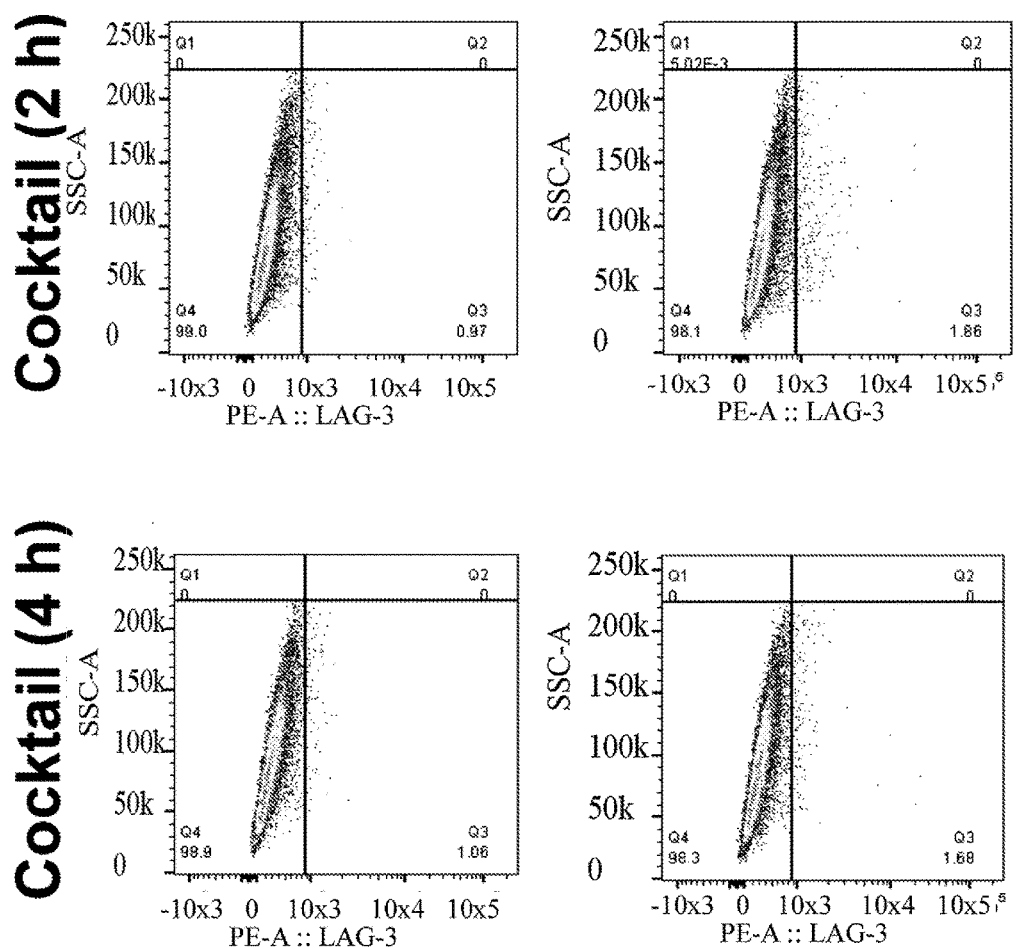

FIG. 4 plots the differential expression of cell surface LAG-3 expression at baseline and following stimulation (0-4 hours) in reference G and risk C expressing cells. Transformed B lymphocytes homozygous for the reference G or risk C alleles were incubated under basal or stimulated cocktail (phorbol ester 500 ng/ml, ionomycin 250 ng/ml, and IL-4 100 U/ml) conditions for 0-4 h and stained with isotype control or anti-LAG-3 antibodies for measurement of cell surface LAG-3, and then fixed for flow cytometry.

Panel I: Reference G-003 cells under basal and stimulated conditions stained with isotype control or LAG-3 antibodies; the data is representative of three independent experiments;

Panel II: Risk C-008 cells under basal and stimulated conditions stained with isotype control or LAG-3 antibodies; the data is representative of three independent experiments.

Figure 5:
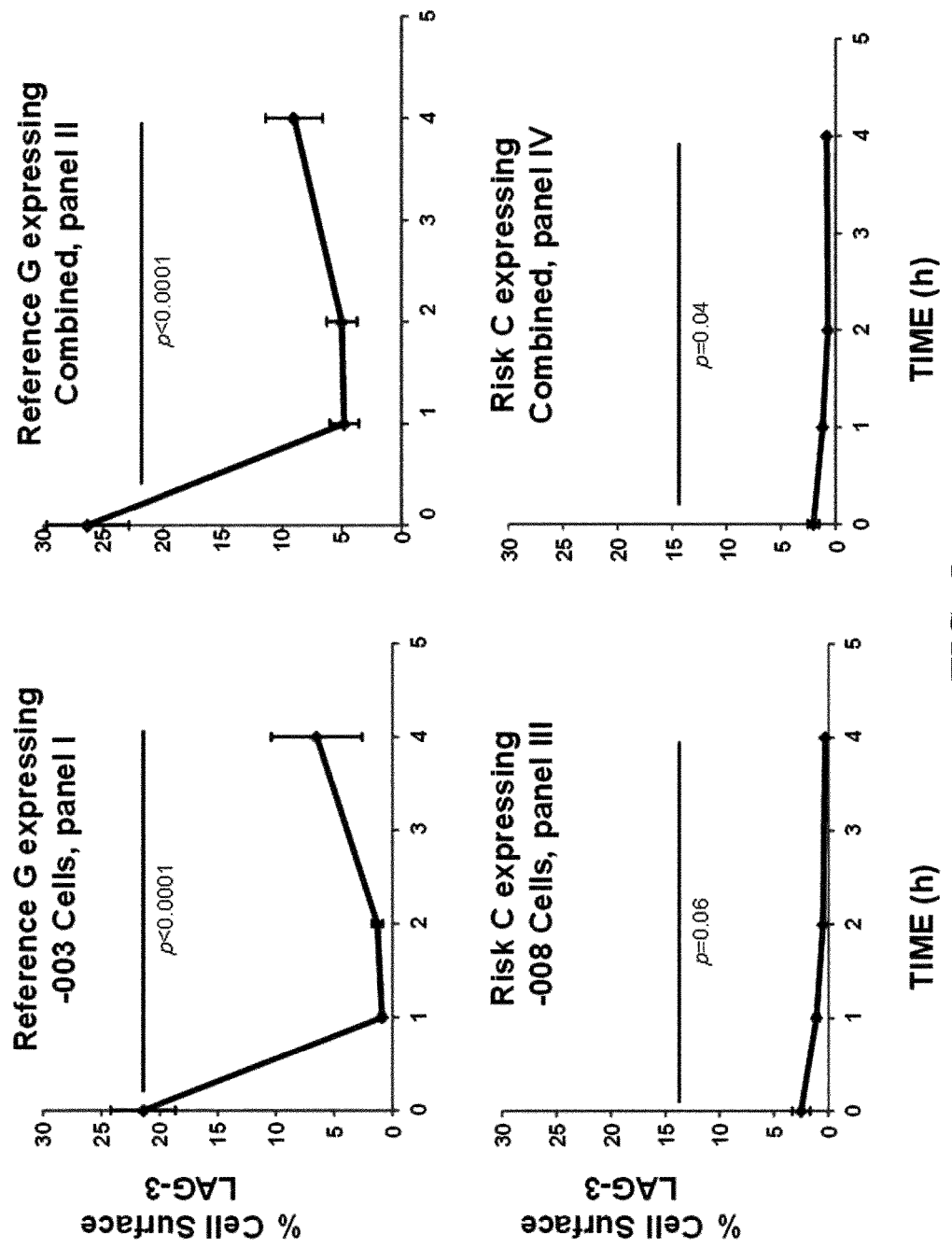
FIG. 5 is a composite of graphs of cell surface expression of LAG-34+ cells as measured by flow cytometry.

FIG. 5 is a graphic analysis of cell surface expression of LAG-3+ cells as measured by flow cytometry.

Panel I represents pooled data (mean±SE) of three independent experiments from the reference G-003 cell lines, each experiment performed with triplicates (n=9, p<0.0001 compared with baseline).

Panel II represents pooled data (mean±SE) from all the reference G cell lines (n=18, p<0.0001 compared with baseline).

Panel III represents pooled data (mean±SE) of three independent experiments from the risk C-008 cell lines, each experiment performed with triplicates (n=9, p=0.06).

Panel IV represents pooled data (mean±SE) from all the risk C cell lines (n=15, p=0.04).

Figure 6:
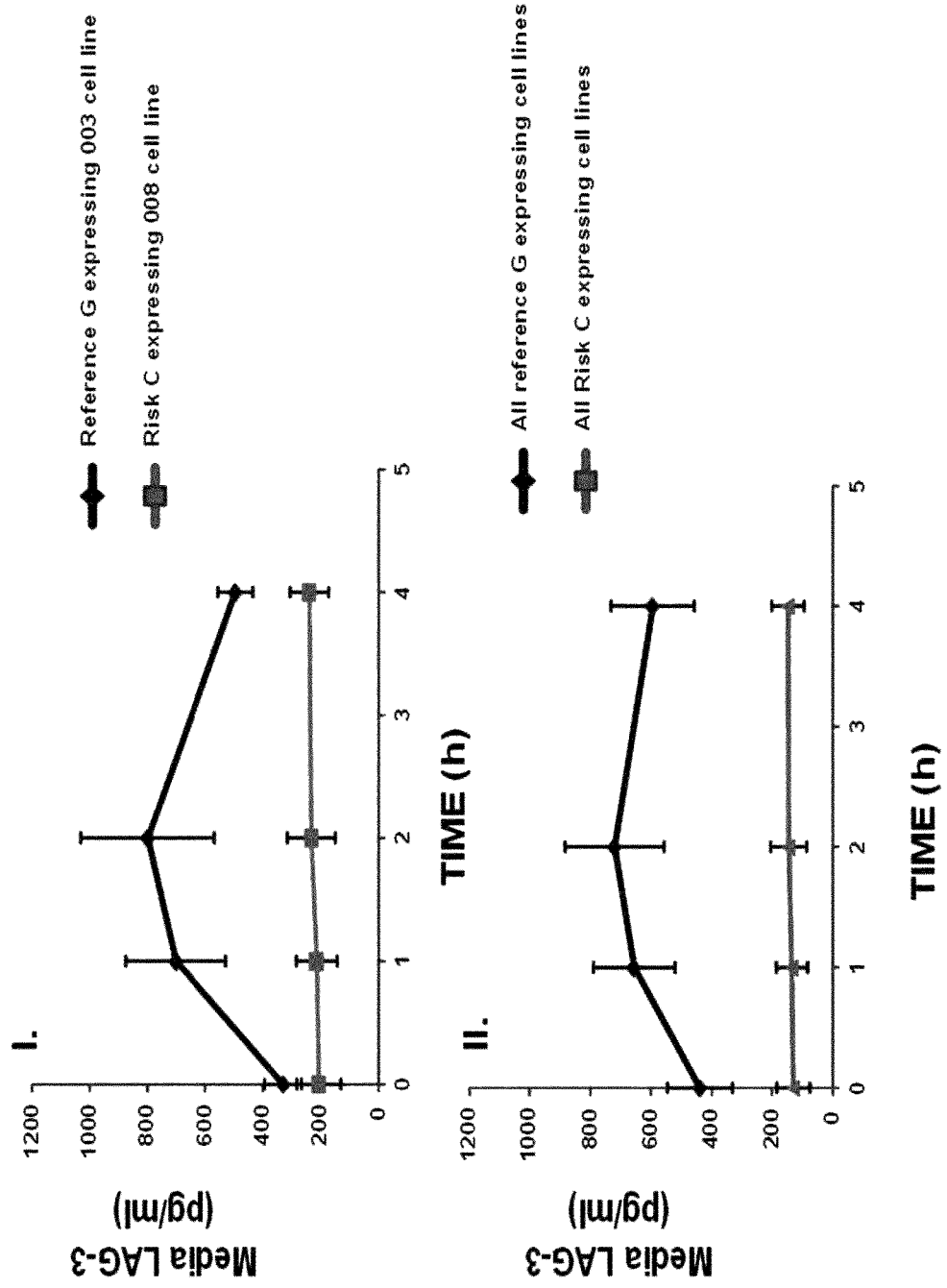
FIG. 6 is a composite of graphs of the changes in LAG-3 levels in the media over time following activation from reference G and risk C expressing cells.

FIG. 6 is a graph of the changes in LAG-3 levels in the media over time following activation from reference G and risk C expressing cells.

Panel I represents pooled data (mean±SE) of three independent experiments from the reference G-003 cell lines, each experiment performed with triplicates (n=9, p<0.0001 compared with baseline), and from pooled data (mean±SE) of three independent experiments from the risk C-008 cell lines, each experiment performed with triplicates (n=9, p=0.06).

Panel II represents pooled data (mean±SE) from all the reference G cell lines (n=18, p<0.000 1 compared with baseline) and pooled data (mean±SE) from all the risk C cell lines (n=15, p=0.04).

Figure 7:
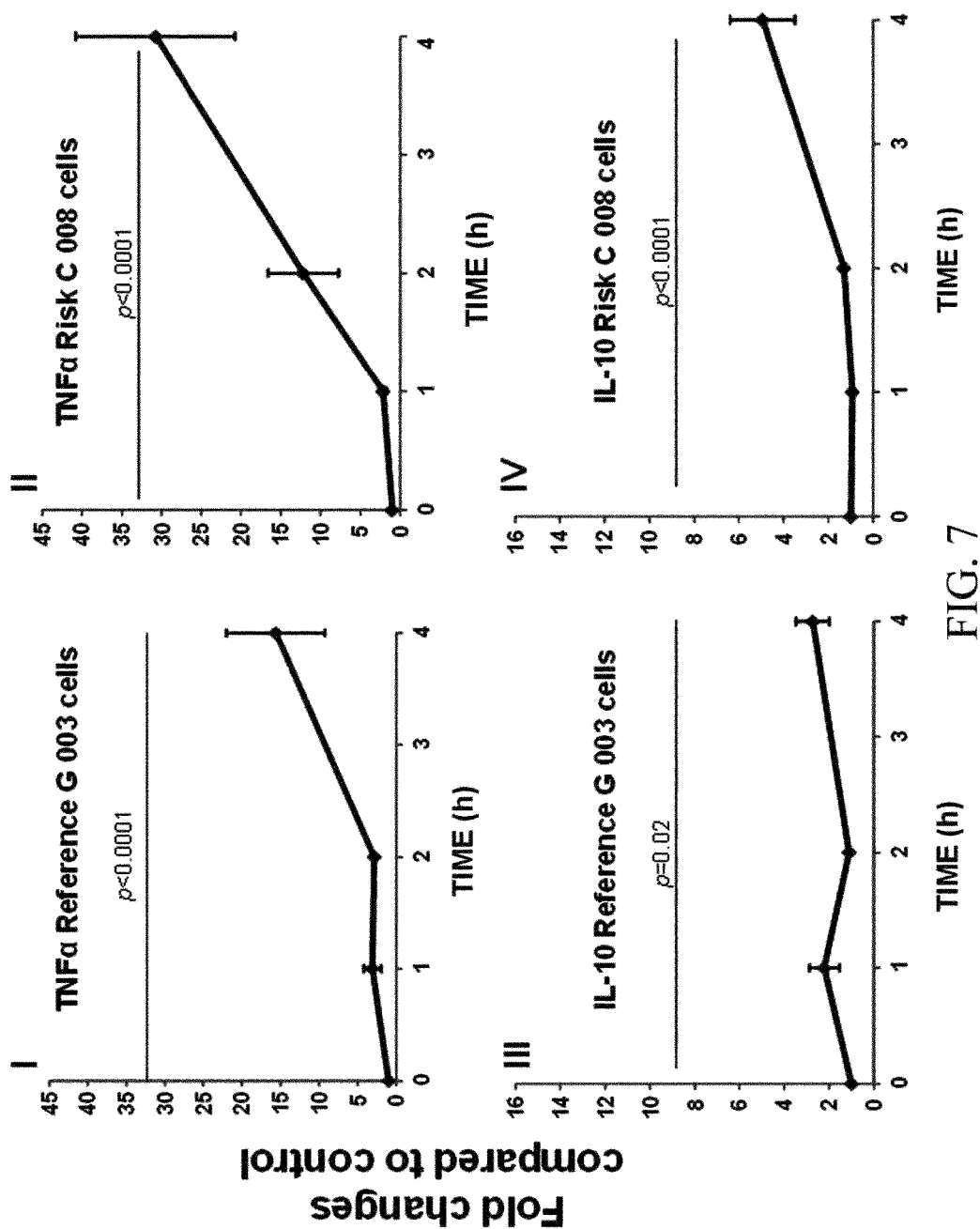
FIG. 7 is a composite of graphs of changes in secreted cytokine (TNFα and IL-10) levels in the media over time following activation in reference G-003 and risk C-008 expressing cells.

FIG. 7 is a graph of changes in secreted cytokine (TNFα and IL-10) levels in the media over time following activation in reference G-003 and risk C-008 expressing cells.

Panel I represents TNFα pooled data (mean±SE) of three independent experiments from the reference G-003 cell lines, each experiment performed with duplicates (n=6, p<0.0001 compared with baseline).

Panel II represents TNFα pooled data (mean±SE) of three independent experiments from the risk C-008 cell lines, each experiment performed with duplicates (n=6, p<0.0001 compared with baseline). Panel III represents IL-10 pooled data (mean±SE) from the reference G-003 cell lines, each experiment performed with duplicates (n=6, p=0.02 compared with baseline), while Panel IV represents IL-10 pooled data (mean±SE) of three independent experiments from the risk C-008 cell lines, each experiment performed with duplicates (n=6, p<0.0001).

As shown in FIGS. 4-5, at baseline, cell surface expression of LAG-3 was 92% lower in the risk C expressing cells (2.02±2.8) as compared with reference G cells (26.3±2.6, p<0.0001). Following stimulation with PMA/ionomycin+IL-4, as compared with baseline levels, over time cell surface LAG-3 expression decreased significantly in reference G (p<0.0001, 003 cell line and all combined) and risk C expressing cells (p=0.06 for 008 cells and p=0.04 for all combined) (FIG. 5). In parallel, over time. LAG-3 levels increased in the medium from the reference G-003 cells (p=0.03, panel I) as compared with no changes observed in the risk C-008 expressing cells (FIG. 6). However, there were no statistically significant differences in LAG-3 media levels when comparing combined G vs. combined C expressing cells (FIG. 6, panel II). Over time TNFα and IL-10 levels in the medium were significantly higher in risk C expressing 008 cells as compared with reference 0 expressing 003 cells (FIG. 7). Expression of LAG-3 is reduced in lipid rafts and downstream signaling is impaired in risk C expressing cells. Since LAG-3 has been shown to localize in lipid rafts in activated cells and affect downstream phosphosignaling, we tested whether this LAG-3 downregulation impacted downstream signaling pathways. Total BCR signaling proteins were detected in all cell lines in the absence of stimulation (FIG. 8(A)).

Figure 8:
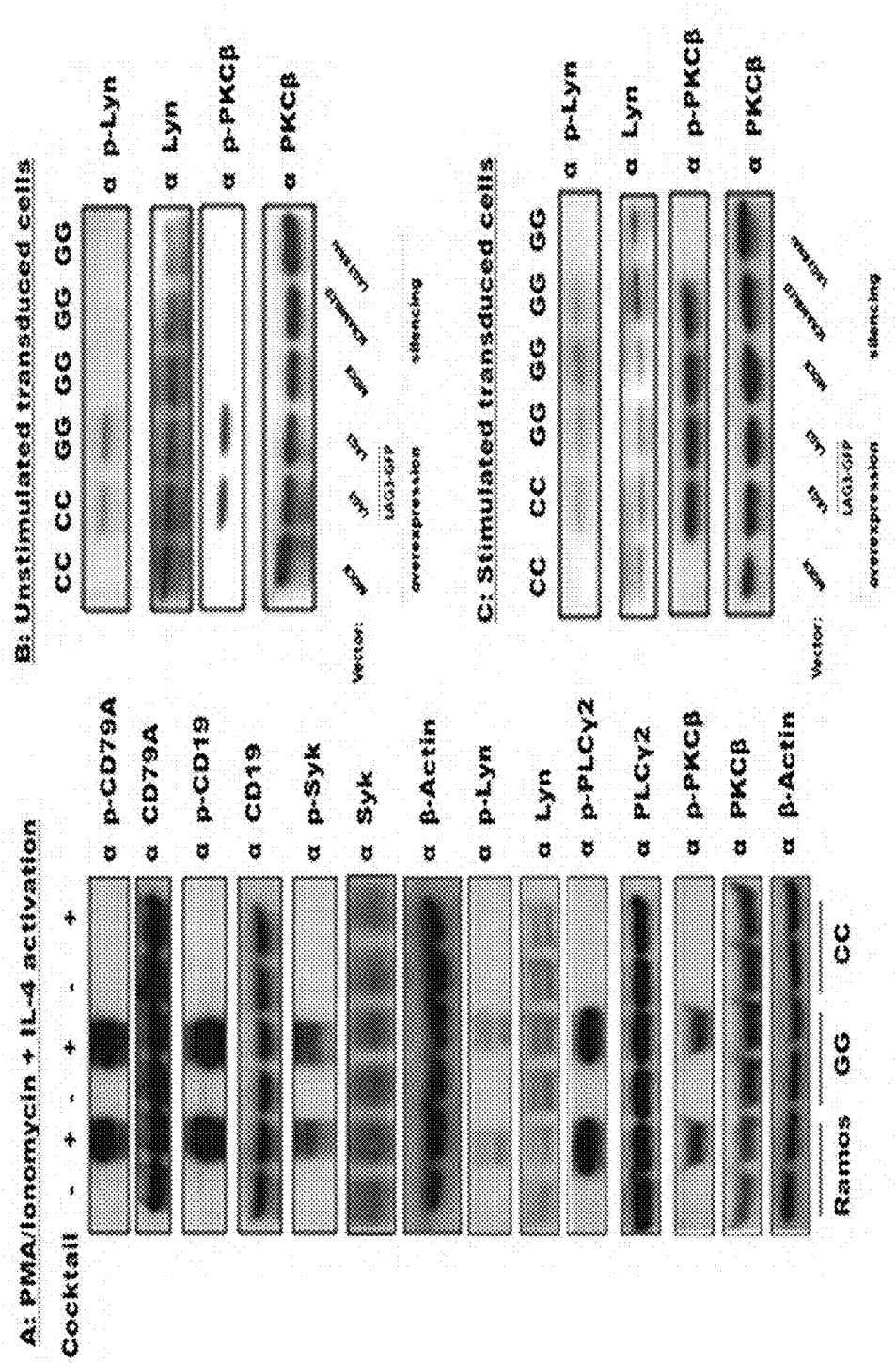
FIG. 8 illustrates by whole cell lysates how LAG-3 is crucial in BCR signaling.

FIG. 8 illustrates how LAG-3 is crucial in BCR signaling. Whole cell lysates were isolated from transformed B cells expressing the reference G or risk C alleles under basal or cocktail stimulated (phorbol ester 500 ng/ml, ionomycin 250 ng/ml, and IL-4 100 U/ml) conditions for 2 h. Reactions were terminated by the addition of an equal volume of lysis buffer and blotted with the indicated total and phospho-antibodies. The results shown are from one representative experiment of 3 replicate pooled samples.

FIG. 8(A): Ramos cell line, GG (003) or CC (008) cells: Stimulated G allele cells, phosphosignaling normalized to corresponding total protein, p-CD79A (p=0.04), p-CD19 (p=0.04), p-Syk (p=0.005), p-Lyn (p=0.001), p-PLCγ2 (p=0.004) and p-PKCβ (p=0.003) as compared with it stimulated conditions in the reference G allele cells.

FIG. 8(B): BCR signaling and overexpression of lentiviral LAG-3-GFP or shRNA-LAG-3 in unstimulated cells: CC cells p-Lyn (p=0.04); p-PKCβ (p=0.03) and GG cells p-Lyn (p=0.04); p-PKCβ (p=0.01) as compared to cells expressing the Mock vector in the respective allele. 2C: BCR signaling and overexpression of lentiviral LAG-3-GFP or shRNA-LAG-3 in stimulated cells: CC cells, p-Lyn (p=0.01); p-PKCβ (p=0.01) in stimulated cells as compared to stimulated cells expressing the Mock vector in the risk C allele. Short-hairpin RNA to knockdown LAG-3 in GG cells, p-Lyn (p=0.002); p-PKCβ (p=0.009) in stimulated cells as compared to stimulated cells expressing the Mock vector in the reference G allele. The results shown are from one representative experiment of 3 replicate pooled samples.

Following stimulation, none of the phosphorylated targets were detected in the risk C expressing cells, while all targets were significantly expressed in the reference G cells compared with the unstimulated condition p-CD79A (p=0.04), p-CD19 (p=0.04), p-Syk (p=0.005), p-Lyn (p=0.001), p-PLCγ2 (p=0.004) and p-PKCβ (p=0.003).

Overexpression or Silencing of LAG-3 Impacts Downstream Signaling Pathways

In order to directly assess the effect of LAG-3 on downstream signaling pathways, we performed experiments wherein LAG-3 was overexpressed in risk C expressing cells (which have decreased LAG-3 levels) or silenced LAG-3 cells in reference G expressing cells that express endogenous LAG-3 protein.

As shown in FIG. 8(B), overexpression of LAG-3 in basal or stimulated risk C cells was associated with significantly increased levels of phosphorylated targets (p=0.04 for p-Lyn; p=0.03 for p-PKCβ in unstimulated cells and p=0.01 for p-Lyn; p=0.01 for p-PKCβ in stimulated cells) as compared with control cells (these being cells that were transfected with an empty vector). Silencing of LAG-3 was associated with significantly lower levels of phosphorylated targets (p=0.002 for p-Lyn; p=0.009 for p-PKCβ in stimulated cells) in the reference G cells as compared with control cells (FIG. 8(C)).

Carriers of the risk C allele had significantly less plasma soluble LAG-3 (sLAG-3). Given that LAG-3 expression and function was reduced in the risk C expressing cells, we next determined if LAG-3 levels would be significantly different in plasma isolated from HALP carriers of the reference G and risk C alleles; this study group constituting the discovery cohort.

Figure 9:
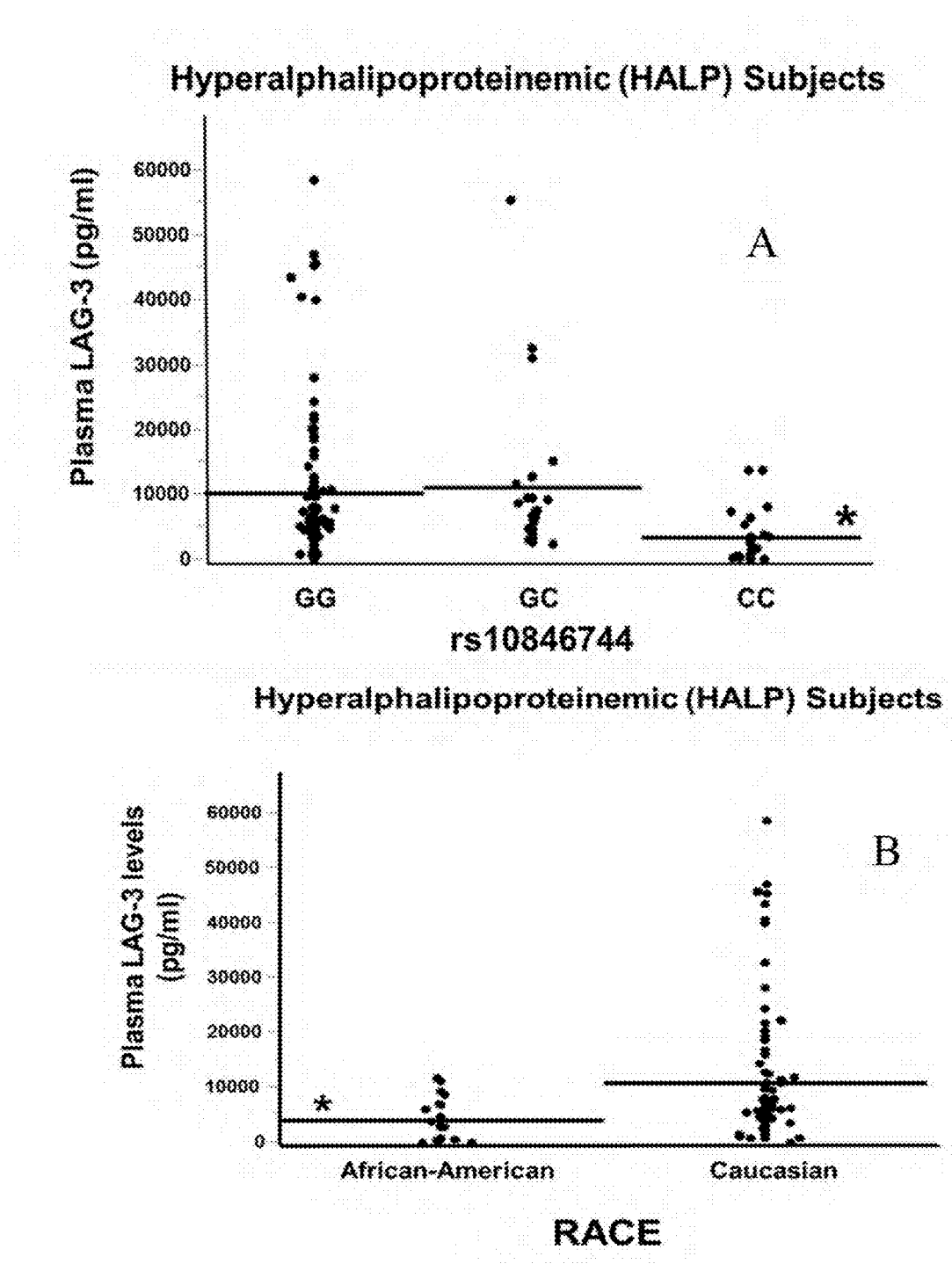
FIG. 9 shows the plasma sLAG-3 levels significantly associated with SCARB1 rs10846744 at (A), and the association of race with plasma sLAG-3 levels at (B).

FIG. 9 shows the plasma sLAG-3 levels significantly associated with SCARB1 rs10846744. As seen in FIG. 9(A), plasma sLAG-3 levels were significantly lower in subjects homozygous for the risk C allele (CC: 3430±2339 pg/ml, n=22, p=0.03) as compared with subjects homozygous for the reference G allele (GG: 10,169±1120 pg/ml, n=96) or heterozygous subjects (GC: 11,139±2288 pg/ml, n=23). We further analyzed the association of race with plasma sLAG-3 levels using data from African-American and Caucasian subjects, since these were the largest percentage of HALP subjects (73% and 17%, respectively [Asians 6% and Hispanics 3%]). As shown in FIG. 9B, plasma sLAG-3 levels were significantly lower in African-Americans (3,902±2493 pg/ml, n=20, p=0.02) compared with Caucasians (10,684±1189 pg/ml, n=88), regardless of rs10846744 genotypes.

Association of Rs10846744 and sLAG-3 with Lipid Subfractions

We next explored the association of rs10846744 and sLAG3 with lipid levels and HDL subfractions. In this HALP population, we did not observe an association of rs10846744 or sLAG-3 with total cholesterol, LDL-C, triglycerides, or HDL-C (data not shown). Likewise, we did not observe an association of rs10846744 or sLAG-3 with plasma apolipoproteins (apoA-I, apoA-II, apoB, apoCI, apoCII, apoC-III, and apoE). We did observe a significant association of rs10846744 with HDL subtractions as measured by NMR spectroscopy.

Figure 10:
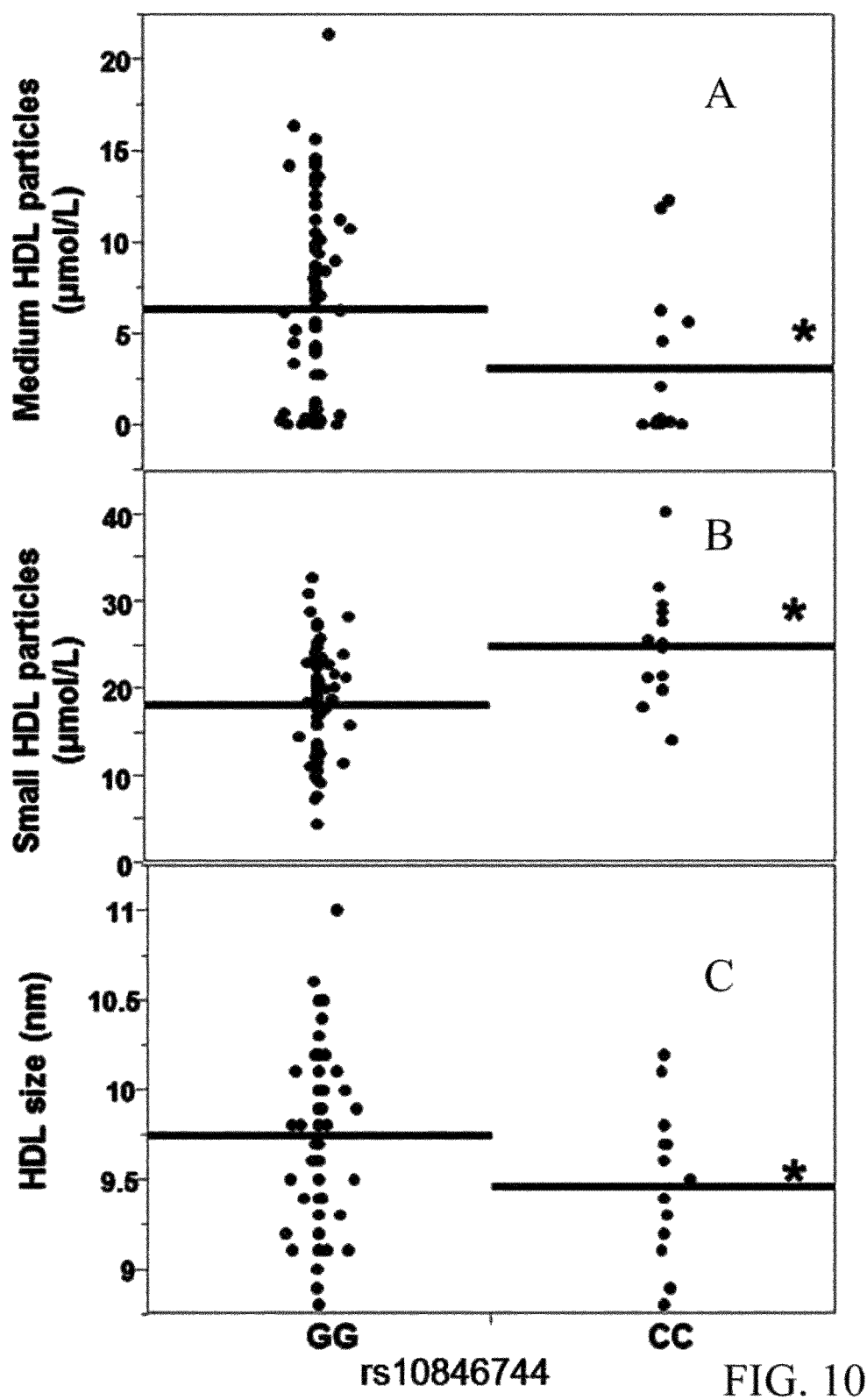
FIG. 10 is a composite of graph showing rs10846744 significantly associated with medium (A), small (B) and total (C) HDL particles as measured by NMR spectroscopy.

FIG. 10 shows rs10846744 significantly associated with medium and small HDL particles as measured by NMR spectroscopy. The medium and small HDL particles were measured by NMR spectroscopy (Liposcience, Raleigh N.C.) in fasting plasma samples isolated from carriers homozygous for the reference G allele and homozygous for the risk C allele for rs10846744. The values shown are mean±standard deviation of medium and small HDL particles (μmol/L) and HDL size (nm).

Panel A: carriers homozygous for the risk C allele had significantly lower levels of medium HDL particles (p=0.04, r=0.2, n=84).

Panel B: carriers homozygous for the risk C allele had higher levels of small HDL particles (p=0.0003, r=0.39, n=84).

Panel C: carriers homozygous for the risk C allele had smaller HDL particle size (p=0.03, r=0.23, n=84).

It can be seen from FIG. 10 that levels of medium size HDL particles (panel A, p=0.04) and total HDL size (panel C, p=0.03) were significantly lower in homozygous carriers of the risk C allele as compared with homozygous carriers of the reference G allele. The concentration of small HDL particles was significantly higher in homozygous carriers of the risk C allele (p=0.0003, r=0.39) as compared with homozygous carriers of the G allele. Consistent with these findings, we observed that plasma LAG-3 levels were inversely associated with small HDL particle concentration, and this data was not stratified by carrier status for rs10846744 (p=0.01, r=0.27, n=81) (FIG. 5).

In conclusion, this establishes the utility of this novel strategy for genotyping to pre-screen for presence of the rs10846744 mutation or inverse correlation to small HDL particles, thereby providing a novel strategy for using LAG-3 expression profiling as a biomarker for assessing inflammasomes, chronic inflammatory diseases and dysfunctional HDL, followed by a tailored therapeutic regimen to mediating said diseases.

EXAMPLE 2

Materials and Methods

The culture medium used in all experiments was RPMI 1640 supplemented with 10% fetal bovine serum (FBS), 100 U/ml penicillin, 100 μg/ml streptomycin (all purchased from Life Technologies, Carlsbad, Calif.). For lymphocyte stimulation, phorbol 12-myristate acetate (PMA) and ionomycin calcium salt were purchased from Sigma-Aldrich (St. Louis, Mo.) while interleukin-4 (IL-4) was purchased from Pepro-Tech (Oak Park, CA). LAG-3 and isotype control fluorophore-conjugated monoclonal antibodies were purchased from Biolegend Inc. (San Diego, Calif.). Antibodies used for signaling were purchased from Cell Signaling Technologies (Beverly, Mass.): anti-CD79A (#3351), anti-phospho CD79A (Y182) (#5173), anti-CD19 (#3574), anti-phospho CD19 (Y531) (#3571), anti-Syk (#2712), anti-phospho-Syk (Y525/526) (#2710), anti-Lyn (#2796), anti-phospho Lyn (Y507) (#2731), anti-PLCγ2 (#3872), anti-phospho-PLCγ2 (Y759)(#3874), anti-phospho-PKCα/β II (T638/641) (#9375). Anti-PKCβ (Santa Cruz Biotechnology, Santa Cruz, Calif. sc-210) and anti-β-Actin (Sigma-Aldrich, St. Louis, Mo.) were purchased separately.

Lymphocytes isolated from HALP subjects were immortalized using Epstein Barr Virus to generate B lymphocytes (University of North Carolina Lineberger Comprehensive Cancer Center Tissue Culture Facility, Chapel Hill, N.C.). EBV transformed B lymphocytes were grown in suspension at density~1-2×10$^6$ cells per ml of complete RPMI 1640 media with L-glutamine, supplemented with 10% FBS and 1% Penicillin-Streptomycin. The media was changed twice a week or more often as needed prior to using cells for experiments.

Total RNA was isolated from three HALP subjects homozygous for the reference G allele and three HALP subjects homozygous for the risk C allele and then subjected to full transcriptome sequencing using the Perkin Elmer next gen sequencing platform (RNA-Seq) (Perkin Elmer, Branford CT). Bioinformatics was performed using Perkin Elmer Gene Sifter software program. The data was adjusted by selecting total map reads, quality reads>20, log transformation, and using Benjamini Hochberg to correct for multiple testing. RNA targets of interest were validated by real-time PCR and western blotting using standard methodologies. RNA-Seq was performed on the separate six cell lines under conditions where cells were cultured in serum (usual culture conditions) and following stimulation with phorbol esters (PMA 500 ng/ml) ionomycin (250 ng/ml), and IL-4 (100 U/ml) for 6 h.

A number of assays were used to assess LAG-3 expression and function in the six EBV-transformed B cell lines.

Flow cytometry: Flow cytometry was performed on as 10-laser flow cytometer (Becton Dickson, Franklin Lakes, NJ). Dead cells were stained with Blue Dead Cell Stain Kit (Molecular Probes, Eugene, Oreg.). To measure the response of LAG-3 in stimulated B cells we first modified and optimized a protocol previously published by Smeland et al. (1). Cells were incubated with and without PMA (500 ng/ml), ionomycin (250 ng/ml) and IL-4 (100 U/ml) for varying time periods (0-4 h). Percent cell surface changes of cell surface LAG-3 expression was calculated by using only the live cell fraction and then subtracting the percent isotype staining values from the percent staining values for cells treated with monoclonal LAG-3 antibodies.

Cytokine secretion into the medium: Levels of interleukin 10 (IL-10) and Tumor Necrosis Factor α (TNFα) were measured in media aliquots isolated from cells cultured under basal and stimulated conditions for varying time periods (0-4 h) by multiplex (Milliplex; Millipore, Temecula, Calif.) on Luminex 200, using XMAP technology.

Western blotting: We used western blotting to measure total and phosphorylated expression of the following proteins known to be involved in downstream signaling in stimulated B cells: p-CD79A, p-CD19, p-Syk, p-Lyn, p-PLCγ2, and p-PKCβ. In some experiments we also stimulated cells with CD40 ligand (CD40L) (200 ng/mL) for 2 h and then isolated whole cell lysates for western blotting. Cells were solubilized with 50 mM Tris-HCl (pH 7.4), 1% NP-40, 0.25% Na deoxycholate, 150 mM NaCl, 1 mM PMSF, 5 mM NaF, 1 mM Na3VO4, 1 mM β-Glycerophosphate, 10 mM Na4P2O7, 2 mM EDTA and complete protease inhibitor cocktail (Roche Diagnostics Corp., San Francisco, Calif.). After 30 minutes of incubation on ice, lysates were clarified by centrifugation (10,000 g) for 15 minutes at 4° C. and supernatants were collected. Protein concentrations were determined using a BCA assay, and equal amounts were subjected to SDS/linear gradient PAGE following solubilization in Laemmli sample buffer. Gel-resolved proteins were subsequently electrotransferred to PVDF membranes via wet tank transfer, which were blocked with 5% nonfat milk prior to antibody incubation. Membranes were then incubated overnight at 4° C. first with antibodies to phospho-proteins, then total proteins. Antibody-antigen complexes were identified by chemiluminescence (ECL+System; Amersham Biosciences, Piscataway, NJ). Anti-β-Actin was used as a loading control. Phosphoproteins were normalized to corresponding total proteins using Image Studio Lite 4.0 for quantification (Licor, Lincoln Nebr.).

Lipid Raft Isolation.

In order to assess expression of LAG-3 in the plasma membrane lipid raft compartment, lipid raft membranes were isolated using 500 mM sodium carbonate (pH 11.0) and sucrose density centrifugation. The sucrose gradient method was performed essentially as described previously (2) with modifications. Cells (1×10$^8$) we e washed with ice-cold PBS and resuspended with 500 mM sodium carbonate, pH 11.0 (2) containing phosphatase and protease inhibitors (1 mM PMSF, 5 mM NaF, 1 mM Na3VO4, 1 mM β-Glycerophosphate, 10 mM Na4P2O7, 2 mM EDTA and Complete protease inhibitor cocktail (Roche Diagnostics Corp., San Francisco, Calif.). The solution was further homogenized with ten strokes in a Wheaton dounce homogenizer. For the discontinuous sucrose gradient, 300 μL of cleared supernatant was mixed with 300 μL of 85% sucrose and transferred to the bottom of a 2.2 mL Beckman centrifuge tube. The diluted lysate was overlaid with 1 ml 35% sucrose and finally 600 μL 5% sucrose. The samples were ultracentrifuged in a Beckman tabletop centrifuge at 70,000 g for 20 h at 4° C. Following centrifugation, gradients were portioned into 10, 220 μL fractions. Fractions 1-3 were pooled (combined fraction 1 on blot), To determine the location of lipid rafts and distinct proteins in the discontinuous sucrose gradient, 40 μL of the raft fractions (4 and 5 of the sucrose gradient, 2 and 3 on blot) and non-raft fractions were subjected to SDS-polyacrylamide gel electrophoresis and immunoblotted.

Overexpression and silencing of LAG-3 assays. We used two experimental approaches to determine if the presence or absence of LAG-3 was causal in altering downstream signaling pathways. We first overexpressed LAG-3 in C expressing cells by transfecting them with lentiviral vectors expressing GFP tagged full-length human LAG-3 cDNA. Our second approach was to use specific shRNA vectors to silence LAG-3 expression in normal G expressing cells.

Lentiviral transfection and transduction: LAG-3-GFP inserted into the pReceiver-Lv122 overexpressing vector, shRNA-LAG-3 inserted into the psi-LVRH1MP RNAi silencing vector, scrambled shRNA, and lentiviral Mock GFP control vectors were obtained from GeneCopoeia (Rockville, Md.). Four shRNA to LAG-3 were screened for selection of the plasmid with the most efficient knockdown. Lentivirus was generated by using Lenti-Pac HIV Expression Packaging Kit (GeneCopoeia, Rockville, Md.). Briefly, 2.5 μl of each individual lentiviral plasmid and 5.0 μl of EndoFectin Lenti reagent were added in Opti-MEM I, to form the DNA-EndoFectine complex. Twenty minutes after incubating the complex at room temperature, the DNA-EndoFectine complex was added to the dish with HEK 293 in DMEM with 10% FBS and incubated in 5% $CO_2$ at 37° C. overnight. The culture medium was replaced with fresh DMEM with 5% FBS and continued to be incubated. The viral-containing culture medium was collected 4 hours post transfection and concentrated after filtration. For transduction with lentivirus, $1\times10^6$ of EBV-transformed B lymphocytes in 1.5 ml of complete media were seeded in a 12-well plate and 500 μl of virus suspension was added. The cells were incubated at 37° C. for 72 h. To assess the effect of either overexpressing LAG-3 in lymphocytes with the risk C allele or silencing LAG-3 in lymphocytes with reference G allele on the downstream signaling pathway, transfected cells were stimulated with and without phorbol esters (500 ng/ml), ionomycin (250 ng/ml) and IL-4 (100 U/ml) cocktail for 2 hours and then processed for western blotting to assess phosphorylation of downstream signaling proteins.

Plasma or soluble lymphocyte activation gene 3 (sLAG-3) assay. sLAG-3 ELISA kits were purchased from RayBiotech, Inc. (Norcross Ga.) and sLAG-3 was measured by first optimizing the kit. Aliquots of fasting plasma samples stored at −80° C. from 143 HALP subjects were thawed, diluted 3-fold, and then 100 μl were used for duplicates per sample for sLAG-3 measurement. The standard curves were diluted 2-fold and yielded linearly associated data. Linear regressions were performed against the standard curve in order to quantify the plasma samples. Values are represented as the mean±standard error.

Again, this established the novel strategy for using LAG-3 expression profiling as a biomarker for assessing inflammasomes, chronic inflammatory diseases and dysfunctional HDL, followed by a tailored therapeutic regimen to mediating said diseases. Further utility is gained by a tailored therapeutic regimen of use of the cholesterol medication probucol, or administering a statin or other cholesterol/lipoprotein altering medication alone or recombinant LAG-3 alone or anti-inflammatory/anti-oxidant alone or in combination with Probucol and/or statin or other cholesterol/lipoprotein altering medication as a therapeutic for atherosclerosis risk in human carriers of the SCARB1 variants rs10846744.

Having now fully set forth the preferred embodiment, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

I claim:

1. A method for detecting dysfunctional HDL cholesterol (HDL-C) in a subject, comprising the steps of:
   (a) detecting the level of soluble lymphocyte activation gene 3 (sLAG-3) protein in a blood sample from the subject;
   (b) comparing the level of sLAG3 in the blood sample with a minimum threshold level of sLAG-3 of ≤3400 pg/ml and determining if plasma levels in said blood sample are less than or equal to said minimum threshold level to detect the presence of dysfunctional HDL-C in the subject;
   (c) determining that there is a comparative deficiency in the level of sLAG-3 versus said minimum threshold wherein said comparative deficiency in the level of sLAG-3 versus said minimum threshold indicates the presence of dysfunctional HDL-C in the subject; and
   (d) treating the subject to improve HDL-C function in the subject with any one or more agents selected from the group consisting of an ant-inflammatory agent, recombinant LAG3, probucol, and a statin.

2. The method of claim 1, wherein the level of HDL-C in the subject is ≥60 mg/dl.

3. The method of claim 1, wherein the level of total cholesterol in the subject is ≥200 mg/dl.

4. The method of claim 1, further comprising a step of pre-screening the subject has one or more risk factors for developing cardiovascular disease and/or immune disease.

5. The method of claim 1, wherein the sample is a serum sample.

6. The method of claim 1, wherein the level of sLAG3 is detected by an immunoassay.

7. The method of claim 6, wherein the immunoassay is ELISA (enzyme-linked immunosorbent assay).

8. A method for determining whether a subject has an increased risk of developing atherosclerosis comprising:
   a) detecting a level of soluble lymphocyte activation gene 3 (sLAG-3) in a sample from the subject;
   b) comparing the level of sLAG-3 in the sample with a minimum threshold level of sLAG-3 of ≤3400 pg/ml and determining if the level of sLAG-3 in the sample is less than or equal to said minimum threshold level;
   (c) determining that there is a comparative deficiency in the level of sLAG-3 protein in the sample when the level of sLAG-3 in the sample is less than said minimum threshold level from said comparing step, wherein said comparative deficiency in the level or sLAG-3 versus said minimum threshold level indicates that the subject has an increased risk of developing atherosclerosis; and
   (d) treating the subject to improve HDL-C function in the subject with any one or more agents selected from the group consisting of an anti-inflammatory agent, recombinant LAG3, probucol, and a strain.

9. The method of claim 8, wherein the level of HDL-C in the subject is ≥60 mg/dl.

10. The method of claim 8, wherein the level of total cholesterol in the subject is ≥200 mg/dl.

11. The method of claim 8, further comprising a step pre-screening the subject for one or more risk factors for developing atherosclerosis.

12. The method of claim 8, wherein the sample is a blood sample.

13. The method of claim 8, wherein the sample is a serum sample.

14. The method of claim 8, wherein the level of sLAG-3 is detected by an immunoassay.

15. The method of claim 8, wherein said immunotherapeutic agent further comprises any other or more agents selected from the group consisting of an anti-inflammatory agent, recombinant LAG-3, an agent that decreases dysfunctional HDL-C in the subject.

16. The method for determining whether a subject has an increased risk of developing atherosclerosis according to claim 8, wherein said first step of detecting a level of soluble lymphocyte activation gene 3 (sLAG-3) in a sample from the subject further comprises genotyping said sample to confirm presence of a subject's underlying rs10846744 SCARB1 mutation.

17. The method for determining whether a subject has an increased risk of developing atherosclerosis according to claim 8, wherein said first step of detecting a level of soluble lymphocyte activation gene 3 (sLAG-3) in a sample from the subject further comprises the substeps of,
(i) measuring small HDL particles in said sample by 2D gel electrophoresis, and
(ii) correlating said measured small HDL particles to sLAG-3 by an inverse correlation of small HDL particles with sLAG-3 indicative of said increased risk.

* * * * *